(12) United States Patent
Baraldi

(10) Patent No.: US 7,976,878 B2
(45) Date of Patent: Jul. 12, 2011

(54) **USE OF WINTER SAVORY (*SATUREJA MONTANA*) OR THE EXTRACTS THEREOF FOR THE PREPARATION OF MEDICAMENTS FOR THE TREATMENT OF THE PREMATURE EJACULATION**

(75) Inventor: Mario Baraldi, Modena (IT)

(73) Assignee: Indena S.p.A., Milan (IT)

( * ) Notice: Subject to any disclaimer, the term of this patent is extended or adjusted under 35 U.S.C. 154(b) by 621 days.

(21) Appl. No.: 11/664,198

(22) PCT Filed: Sep. 28, 2005

(86) PCT No.: PCT/EP2005/010481
§ 371 (c)(1),
(2), (4) Date: Dec. 10, 2007

(87) PCT Pub. No.: WO2006/037535
PCT Pub. Date: Apr. 13, 2006

(65) Prior Publication Data
US 2008/0199542 A1    Aug. 21, 2008

(30) Foreign Application Priority Data
Oct. 1, 2004  (IT) .......................... MI2004A001871

(51) Int. Cl.
*A61K 36/00*    (2006.01)

(52) U.S. Cl. ....................................... 424/725

(58) Field of Classification Search .................. None
See application file for complete search history.

(56) References Cited

U.S. PATENT DOCUMENTS 6,140,363 A * 10/2000 Hur et al. ....................... 514/533
2002/0103414 A1* 8/2002 Harrison et al. ................ 600/29

OTHER PUBLICATIONS

Dr. James Duke: Chemicals in *Satureja montana* L. (Lamiaceae)--Savory, Winter Savory; Phytochemical and Ethnobotanical Databases [online] URL<http://www.ars-grin.gov/cgi-bin/duke/farmacy2.pl>, pp. 1-4, accessed Apr. 5, 2010.*
Phillipson, J. New Drugs From Nature—It Could Be Yew; Phytotherapy Research 13 (1999) pp. 2-8.*
Revilla et al. Comparison of Several Procedures Used for the Extraction of Anthocynains From Red Grapes; J. Agric. Food Chem. 1998, 46, pp. 4592-4597.*
Pepeljnjak S. et al., "Antimicrobial Activity of the Ethanolic Extract of *Satureja montana* Sp. Montana", Acta Pharmaceutica, Zagreb, HR 49(I):65-69 (1999).
Lena Santos, "*Satureja montana*" [Online] 2004, Retrieved from the Internet: URL:http://home.swipnet.se/{w-47128/efile6.htm>.
Michael Weishan, "World of Gardening," [Online] 1998, Retrieved from the Internet: URL:www.michaelweishan.com/tradegdnspr98art3.html>.
Angelini et al., "Essentail Oils from Mediterranean Lamiaceae as Weed Germination Inhibitors", J Agri Food Chem, Am Chem Soc, 51:6158-6194 (2003).
Sefidkon et al., "Chemical Composition of the Essential Oil of Three Iranian Satureja Species (*S. Mutica, S. Macrantha* and *S. Intermedia*;", Food Chem, Elsevier Sci Pub Ltd., GB., 91(1):1-4 (2005).

* cited by examiner

*Primary Examiner* — Patricia Leith
(74) *Attorney, Agent, or Firm* — Porzio, Bromberg & Newman, P.C.

(57) ABSTRACT

The use of Winter savory or its purified extracts rich in rosmarinic acid, the use of rosmarinic acid and the extracts containing it for the preparation of medicaments for the treatment of premature ejaculation.

2 Claims, No Drawings

USE OF WINTER SAVORY (*SATUREJA MONTANA*) OR THE EXTRACTS THEREOF FOR THE PREPARATION OF MEDICAMENTS FOR THE TREATMENT OF THE PREMATURE EJACULATION

The present invention relates to the use of Winter savory or purified extracts thereof rich in rosmarinic acid, and the use of rosmarinic acid or extracts containing it for the preparation of medicaments for the treatment of premature ejaculation.

TECHNOLOGICAL BACKGROUND

Premature ejaculation, which is ejaculation occurring before the individual wishes, is a dysfunction affecting more than 30% of male population, mainly adolescent, but that may also persist in the adult. Three main causes are apparently involved:

1) organic factors, such as anatomical or physiological alterations of the reproductive system;
2) psychological factors, deriving from wrong sexual education or deep-seated problems related to improper sexual development during growth;
3) external factors, such as use of drugs (amphetamines, hallucinogens), excessive consumption of alcoholics, food and medications.

Premature ejaculation can ultimately be ascribed to alterations of the neuroconduction and neuromodulation processes which modulate the sexual behaviour both at the central and peripheral levels. Therefore, pharmacological treatment usually consists in the administration of benzodiazepines (alprazolam 0.25 mg), antidepressants acting on the serotoninergic system (paroxetine 20 mg), or in the local application of anaesthetics (prilocaine 25 mg+lidocaine 25 mg).

As this type of therapy does not always prove effective and also involves side effects such as sedation or cardio circulatory problems, there is the need for novel active principles.

It has now been found that Winter savory (*Satureja montana*) or the extracts thereof, as well as rosmarinic acid or the extracts containing it, can be used for the preparation of medicaments for the treatment of premature ejaculation.

DETAILED DISCLOSURE OF THE INVENTION

Winter savory (*Satureja montana*) is a plant belonging to the Lamiaceae family, already known in traditional medicine as a remedy against asthenia or as aphrodisiac.

The object of the invention is the use of Winter savory or the extracts thereof, and of rosmarinic acid or extracts containing rosmarinic acid, for the preparation of medicaments for the treatment of premature ejaculation.

The invention further relates to a Winter savory total extract useful for the preparation of medicaments for the treatment of premature ejaculation.

A further object of the invention is the use of rosmarinic acid or extracts containing it for the preparation of medicaments for treatment of premature ejaculation.

According to the invention, the process for the preparation of the Winter savory purified extract comprises the following steps:

a) milling Winter savory dried aerial parts;
b) extracting them one or more times with water and recovering the extraction solvent;
c) filtering the extraction solvent or the combined extraction solvents and subsequent hot concentration under reduced pressure to obtain a concentrated solution;
d) eluting the concentrated solution from step c) on a resin column;
e) washing the resin with water;
f) eluting with ethanol;
g) hot concentrating the organic phase under reduced pressure;
h) drying the resulting syrup under vacuum at 60° C. for 24 hours;
i) milling the resulting solid.

Alternatively to steps d)-f), the solution from step c) is extracted once or repeatedly with butanol; the organic phase (or combined organic phases) is then subjected to steps g), h) and i).

The resulting extract was solubilised in Tween 80 (10%) and water and administered to test animals through a gastric probe, in a volume of 5 ml/kg, at different doses, 45 minutes before the in vivo test.

After acute administration per os (25, 50 and 100 mg/kg), a statistically significant increase in ejaculation latency has been observed.

HPLC analysis of Winter savory purified extract evidenced the presence of rosmarinic acid that, when tested under the same experimental conditions at doses of 10 and 20 mg/kg, showed equivalent activity to that of the extract.

Qualitatively similar, although quantitatively different, results were obtained replacing the purified extract with the total aqueous extract of Example I and with the alcoholic extract of Example IV.

For the treatment in humans, the compounds of the invention can be incorporated in pharmaceutical formulations suitable for the oral, intramuscular, transdermal administrations, with conventional excipients and methods. Doses can range from 100 mg to 2000 mg daily, preferably from 200 to 400 mg daily.

The invention is described in more detail by the following examples.

Example I

Preparation of Total Aqueous Extract

One kg of finely ground *Satureja montana* dried leaves is extracted by infusion at 70° C. with 4 volumes of water for 4 hours. The procedure is repeated for 5 times. The hot extracts are filtered, combined and concentrated under vacuum to give a soft extract, which is subsequently dried under vacuum at 60° C. to give 290 g of dry extract.

Example II

Purification of Total Aqueous Extract with Butanol 100 g of the extract of Example I is redissolved in 10 volumes of water. The solution is extracted at room temperature with 3×0.5 litres of water-saturated n-butanol. Combined butanolic extracts are concentrated to a soft extract. The butanol residue is replaced with water. The extract is dried under vacuum at 60° C. to give 11 g of a dry extract with 9.74% content in rosmarinic acid.

Example III

Purification of Total Aqueous Extract with Adsorbing Resins 50 g of the extract of Example I is redissolved in 10 volumes of water, absorbed on a column containing 1 litre of duolite XAD761, and washed with 5000 ml of water. Washings are discarded and the column is eluted with 3000 ml of 95% ethanol. The hot ethanol fraction is concentrated under reduced pressure to obtain a soft extract which is subsequently dried under vacuum at 60° C. for 24 hours. 5 g of purified extract is obtained, having 10.48% content in rosmarinic acid.

Example IV

Preparation of Winter Savory Alcoholic Extract

Dried aerial parts of Winter savory (100 g) are macerated in 500 ml of 90% (v/v) ethanol for 24 hours; the suspension is then filtered and evaporated to dryness.

Example V

Copulatory Activity

Sprague-Dawley rats were used, both males (weighing approx. 220 g) and females (weighing approx. 160 g), from Harlan Italy (Udine, Italy). The animals were housed under controlled temperature and humidity conditions (22±1° C., 60% humidity), with 12 hours inverted light-darkness cycle, with lights on at 7 a.m. Females were ovariectomized and subcutaneously injected with estradiol valerate (500 μg) and progesterone (2 mg) 48 hours after, to induce estrus. Male rats with very short ejaculation latency time were chosen through starting screening consisting of 7 pre-tests [A. Ågmo, Male rat sexual behavior, *Brain Research Protocols* 1: 203-209, 1997].

The resulting extract according to Example II or rosmarinic acid were solubilised in Tween 80 (10%) and water and administered to animals, by gastric probe, in a volume of 5 ml/kg, at different doses, 45 minutes before carrying out all the in vivo tests.

Sexual behaviour was evaluated under quite conditions, with feeble red light, according to the standard procedure [A. Ågmo, Male rat sexual behavior, *Brain Research Protocols* 1: 203-209, 1997]. The main parameters recorded during the test were:
1) mount latency (ML);
2) intromission latency (IL);
3) ejaculation latency (EL);
4) postejaculatory interval (PEI);
5) mount frequency (MF);
6) intromission frequency (IF).

Results

Table 1 shows that all of the doses of Winter savory extract administered (25, 50, and 100 mg/kg) induced slowing down of the copulatory activity, and a statistically significant prolonging of ejaculation latency. The same results were obtained with rosmarinic acid at doses of 10 and 20 mg/kg (Table 2).

TABLE 1

Effect of the administration of Winter savory extract on copulatory activity

| Treatment (mg/kg) | ML (sec) | MF (n°) | IL (sec) | IF (n°) | EL (sec) | PEI (sec) |
|---|---|---|---|---|---|---|
| Control | 155.0 ± 41.7 | 2.5 ± 0.5 | 155.1 ± 41.7 | 21.0 ± 3.2 | 469.2 ± 80.2 | 392.2 ± 20.4 |
| Winter savory 25 | 499.7 ± 132.8* | 1.2 ± 0.2** | 499.8 ± 132.7* | 23.8 ± 3.6 | 1420.0 ± 215.9* | 686.7 ± 101.7* |
| Control | 247.5 ± 42.1 | 3.1 ± 0.6 | 283.1 ± 48.2 | 27.8 ± 3.8 | 496.0 ± 107.4 | 508.6 ± 67.2 |
| Winter savory 50 | 451.1 ± 130.0 | 1.2 ± 0.2* | 451.1 ± 130.0 | 29.6 ± 4.7 | 1346.0 ± 161.7* | 562.0 ± 127.0 |
| Control | 37.7 ± 13.2 | 8.9 ± 0.5 | 73.6 ± 26.2 | 12.7 ± 0.7 | 470.4 ± 10.9 | 301.9 ± 6.6 |
| Winter savory 100 | 160.4 ± 88.8 | 6.2 ± 1.1 | 189.2 ± 86.4 | 9.5 ± 0.8* | 1552.2 ± 208.9 | 458.2 ± 74.2*** |

Values are expressed as mean ± SEM (n = 8-10).

Mann-Whitney test:

*p < 0.05,

**p < 0.01,

***p < 0.001 vs. the respective controls.

TABLE 2

Effect of the administration of rosmarinic acid on copulatory activity

| Teatment (mg/kg) | ML (sec) | MF (n°) | IL (sec) | IF (n°) | EL (sec) | PEI (sec) |
|---|---|---|---|---|---|---|
| Control | 135.2 ± 33.4 | 2.4 ± 0.3 | 147.1 ± 37.5 | 22.3 ± 3.9 | 483.3 ± 60.6 | 383.1 ± 18.3 |
| Rosmarinic acid 10 mg/kg | 382.4 ± 93.6* | 1.6 ± 0.3 | 393.9 ± 89.8* | 19.8 ± 1.2 | 1282.2 ± 90.4* | 548.5 ± 45.5* |
| Control | 184.3 ± 45.3 | 2.9 ± 0.3 | 199.7 ± 37.3 | 24.1 ± 2.3 | 470.9 ± 71.1 | 444.4 ± 6.6 |
| Rosmarinic acid 20 mg/kg | 425.8 ± 83.2* | 1.1 ± 0.1* | 408.4 ± 48.6* | 27.3 ± 0.7 | 1493.1 ± 81.9** | 602.2 ± 102.4* |

Values are expressed as mean ± SEM (n = 8-10).
Mann-Whitney test:
*p < 0.05,
**p < 0.01, vs. respective controls.

CONCLUSIONS

The results reported above prove that the Winter savory purified extract acts on copulatory activity, significantly prolonging the ejaculation time. The effect is dose-dependent after oral administration and appears after 30-45 minutes.

The invention claimed is:

1. A method of treating premature ejaculation comprising orally administering, to a person in need thereof, a medicament comprising an effective amount of isolated rosmarinic acid for treating premature ejaculation.

2. A method for treating premature ejaculation comprising orally administering a medicament comprising an effective amount of active to a subject in need thereof, the active comprising an extract containing rosmarinic acid, said extract containing rosmarinic acid being prepared by:

extracting *Satureja Montana* dried leaves one or more times with water and recovering first extract(s);

filtering the first extract(s) and subsequent hot concentration of the first extract(s) under reduced pressure to obtain a concentrated extract solution;

drying the concentrated extract solution to obtain a dried extract;

dissolving the dried extract in water and recovering an aqueous second extract;

extracting the aqueous second extract with water saturated n-butanol and recovering an n-butanol extract;

concentrating the n-butanol extract to remove the n-butanol and adding water to the concentrate, and drying the n-butanol extract concentrate wherein the dried n-butanol extract is said active.

* * * * *